United States Patent [19]
Barnes

[11] Patent Number: 5,207,233
[45] Date of Patent: May 4, 1993

[54] ULTRA-VIOLET RAY SHIELD

[76] Inventor: Bradley L. Barnes, 7131 Owensmouth, A 96, Canoga Park, Calif. 91303

[21] Appl. No.: 867,386

[22] Filed: Apr. 13, 1992

[51] Int. Cl.⁵ ............................ A61F 6/02; A61F 5/37
[52] U.S. Cl. ..................................... 128/842; 128/846
[58] Field of Search ............... 128/846, 842, 844, 917, 128/918; 604/330, 247–353; 2/401, 402, 403, 406; 450/132, 133, 153

[56] References Cited
U.S. PATENT DOCUMENTS

| | | | |
|---|---|---|---|
| 2,577,345 | 12/1951 | McEwen | 128/844 |
| 3,310,053 | 3/1967 | Greenwood | 128/830 |
| 3,648,700 | 3/1972 | Warner | 128/844 |
| 4,590,931 | 5/1986 | Kidwell | 604/349 |
| 4,604,998 | 8/1986 | Bellina | 128/849 |
| 4,611,588 | 9/1986 | Laptewicz | 128/846 |
| 4,685,913 | 8/1987 | Austin | 604/349 |
| 4,875,491 | 10/1989 | Parrone | 128/844 |
| 4,942,885 | 7/1990 | Davis | 128/844 |
| 4,971,074 | 11/1990 | Hrubetz | 604/349 |
| 5,048,541 | 9/1991 | Haneline | 128/842 |

Primary Examiner—Robert A. Hafer
Assistant Examiner—Michael Brown
Attorney, Agent, or Firm—Roger A. Marrs

[57] ABSTRACT

A flexible shield is disclosed herein having an open-ended pouch for covering certain soft tissue areas of a person undergoing a tanning procedure on a conventional tanning couch or bed. The shield is composed of a layered construction with an interlayer composed of a vinyl impregnated with lead particles and an outer layer of a covering cloth. An inner layer is of cushion material adapted to contact the soft tissue body area of the user. The pouch may include a slit so that the layered construction may be overlapped to accommodate size or area intended to be covered. A hook and pile closure serves as a detachable fastener for retaining the pouch in its operative position. The shield may be used by men or women.

1 Claim, 1 Drawing Sheet

ULTRA-VIOLET RAY SHIELD

BACKGROUND OF THE INVENTION

1. Field of the Invention

The present invention relates to the field of ultra-violet ray shields, and more particularly to a novel shield for protecting the soft body tissues of a person undergoing a tanning procedure from the adverse effects of ultra-violet rays.

2. Brief Description of the Prior Art

In the past, it has been the conventional practice for sunbathers to spend a substantial amount of time exposed to direct sunlight in order to raise the melanin levels in the skin tissue so as to obtain a tanning effect. In order to more conveniently obtain this effect, it is now the common practice to employ tanning beds which employ ultra-violet ray lamps to which the user of the apparatus subjects his or her skin for tanning purposes. In both natural sunlight and in the use of the ultra-violet ray beds, recent research has revealed that the soft body tissues of the human body are adversely affected by ultra-violet rays and, in many instances, it is believed that cancer develops.

Attempts have been made when using tanning beds to protect certain areas of the body from the ultra-violet rays such as by employing goggles for covering the eyes or in some instances, a towel or other cotton fabric material which can be draped or worn over sensitive areas of the body. However, it is believed that the ultra-violet rays penetrate cotton fabric so as to reach the sensitive body areas and, therefore, such cloth is not effective for protective purposes.

Therefore, a long-standing need has existed to provide a simple and effective means for protecting the soft body tissues of a person using conventional tanning beds which employ ultra-violet ray generators for creating a tan on the skin of the user. Such a means should be convenient to use and must be a positive block for ultra-violet rays so that such rays will not penetrate the shield and cause tissues to be damaged.

SUMMARY OF THE INVENTION

Accordingly, the above problems and difficulties are obviated by the present invention which provides a novel shield composed of material of sandwich construction which includes a central or interlayer composed of vinyl plastic impregnated with lead particles so as to be impervious to ultra-violet rays. One side of the interlayer is provided with a cloth covering while an inner layer adapted to be adapted adjacent the skin of the user will be of a cushion composition. The various layers are joined by conventional means such as adhesive, stitching or the like. In one form of the invention, the means takes the form of a shield pouch which is open-ended in order to receive the selected soft tissue member, such as the genitals of a male user, and which includes a retaining means for adjusting the shield for form and size. In another form, the shield may be a sheet of the aforementioned sandwich construction material which is draped or placed over the soft tissue areas of the user and such a means is more adapted for female usage.

Therefore, it is among the primary objects of the present invention to provide a novel means for protecting soft body tissues of a person undergoing a tanning procedure from being adversely affected by ultra-violet rays.

Another object of the present invention is to provide a novel shield that may be readily worn or draped over the soft body tissues of the user to protect the tissues from ultra-violet radiation.

Still a further object of the present invention is to provide a relatively inexpensive and novel means whereby a person using a tanning bed may conveniently protect soft body tissues from adverse effects of ultra-violet radiation.

BRIEF DESCRIPTION OF THE DRAWINGS

The features of the present invention which are believed to be novel are set forth with particularity in the appended claims The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
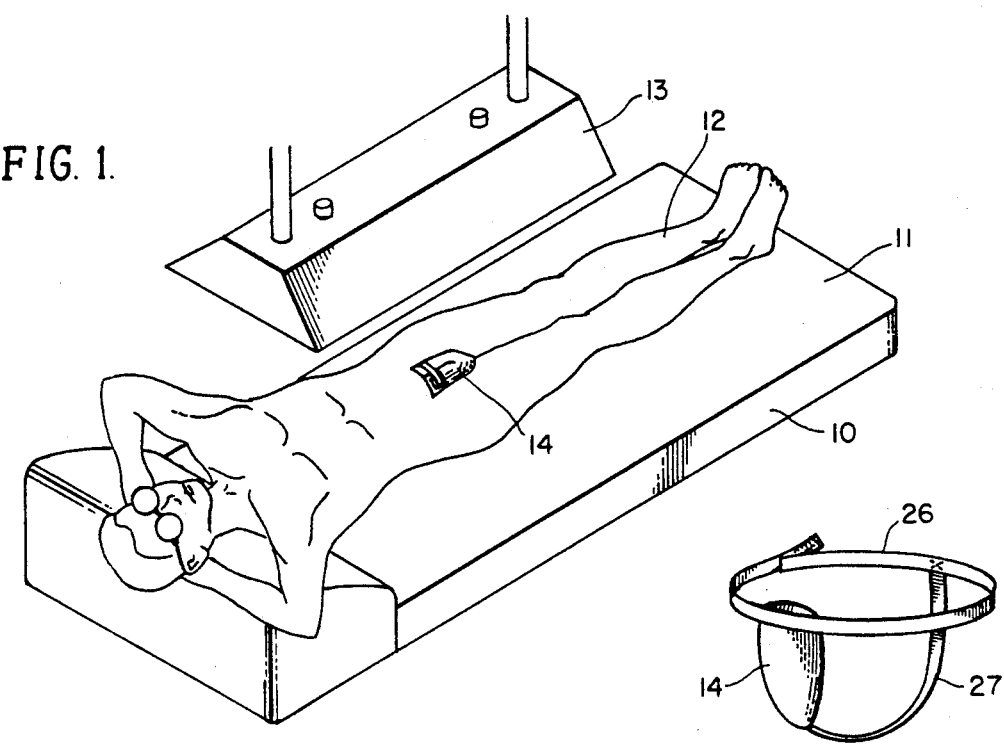
FIG. 1 is a front perspective view of a person utilizing a tanning bed and employing the protective shield of the present invention.

Referring to FIG. 1, a conventional tanning bed is indicated by the numeral 10 which includes a couch 11 on which the user 12 reclines during a tanning procedure. A lamp assembly 13 serves as a source of ultra-violet rays to which the user 12 is subjected. Many of the body areas include soft tissue and such an area is represented by the genitals of the male. The subject invention is indicated by numeral 14 and is employed for covering or holding the genitals for protection purposes during the tanning procedure. The invention takes the form of a shield 14 which protects the soft body tissues from bombardment by ultra-violet radiation and blocks or interferes with the ultra-violet rays as they are applied to the body surface of the user 12.

Figure 2:
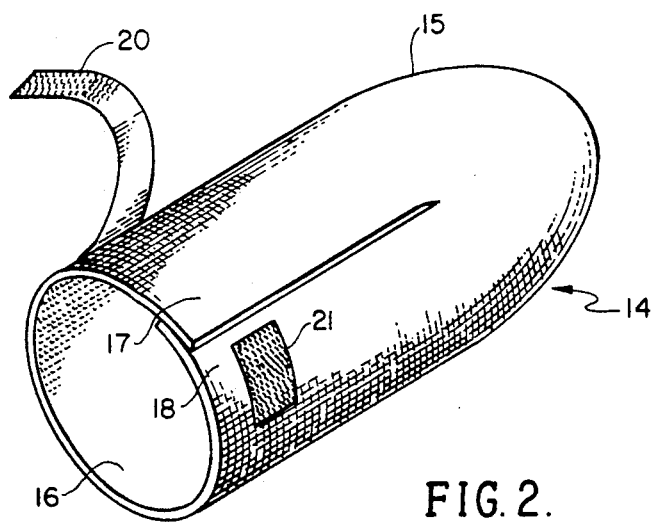
FIG. 2 is an enlarged perspective view of the novel shield worn by the person shown in FIG. 1.

Referring now in detail to FIG. 2, it can be seen that the shield 14 includes an elongated pouch 15 which is open at end 16 so that body portions of the user may be inserted into the pouch. Portions 17 and 18 of the pouch adjacent the opening 16 include a dividing slit so that the material of the pouch at the open end may be overlapped to accommodate size or proportion of body parts introduced into the pouch. In order to retain the pouch in proper position, a closure means is employed to releasably fasten the pouch to the user which may take the form of a hook and pile fastener, represented by numeral 20 for the hook portion and numeral 21 for the pile portion of the closure. It is to be understood that the shield or pouch 14 is composed of pliable material which will not scratch, encumber or restrict the user during the tanning procedure.

Figure 3:
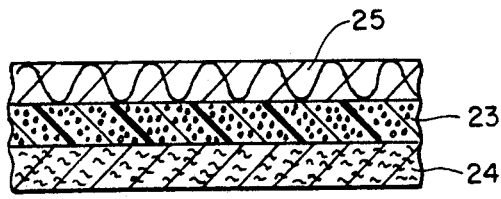
FIG. 3 is a transverse cross-sectional view of the shield showing the multi-layer sandwich construction.

Referring now in detail to FIG. 3, it can be seen that an enlarged cross-section of the shield or pouch 14 includes an interlayer 23 which is composed of vinyl impregnated with lead particles so as to block passage of ultra-violet radiation. One side of the interlayer 23 is attached with a covering cloth 24 that constitutes an outer layer while an inner layer 25 is of a cushion composition and is intended to contact against the immediate skin of the user at the soft body tissue area.

Figure 4:
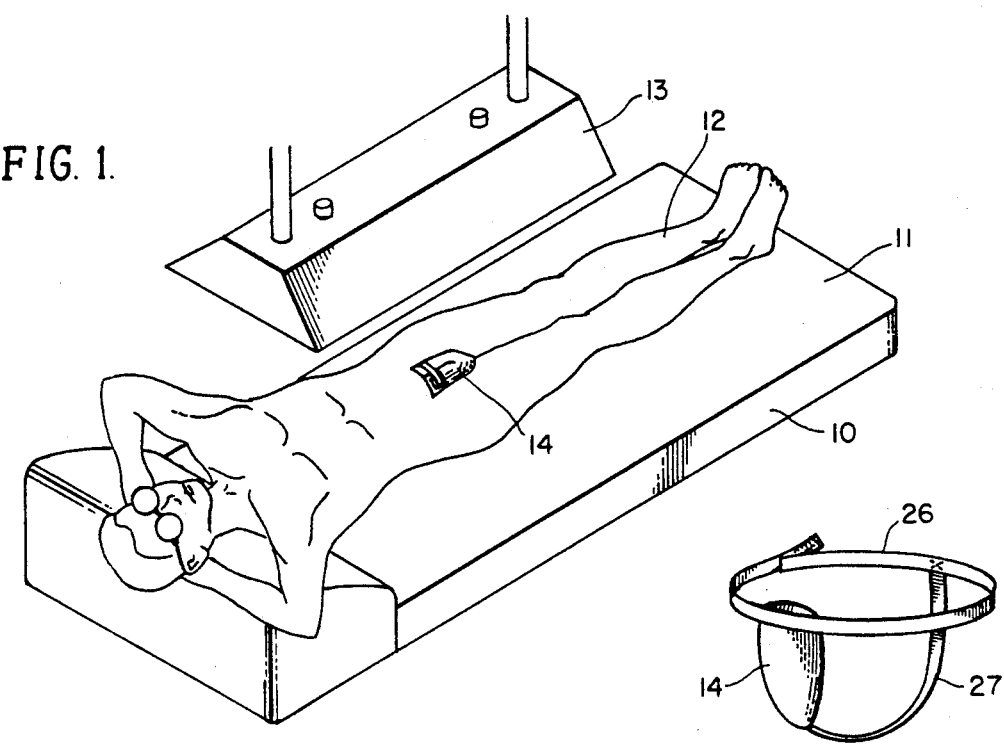
FIG. 4 is a perspective view of another version of the present invention showing waist and leg straps for retaining the shield in position on the body of the user.

Referring now in detail to FIG. 4, another embodiment of the invention is illustrated wherein the shield or pouch is indicated by numeral 14 and waist straps and leg straps are illustrated and represented by numerals 26 and 27 respectively. When using this embodiment, the user's legs will be inserted through the leg straps while the waist strap encircles the waist of the user.

It is envisioned that the present invention may also be used by women where the soft tissue body areas are covered by a sheet of the material shown in FIG. 3. Also, the pouch as shown in FIG. 2 may be employed in a flattened manner and used in a sheet form for covering the sensitive areas of a woman's body so as to block passage of ultra-violet radiation.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A shield effective against ultra-violet radiation comprising:
   a shield of three-layered material carried together as an integral construction;
   said three-layered construction including an interlayer composed of a vinyl material impregnated with lead particles, an outer material layer composed of a cloth fabric and an inner layer composed of a cushion material;
   said shield is an open-ended pouch having a hook and pile fastener for releasably retaining said pouch opening in a closed position;
   said pouch includes an adjustable slit separating adjacent overlapping edge marginal regions and disposed at said open end to permit overlap edge marginal regions of said pouch for sizing and convenience;
   adjustable strap means attached to said pouch for accommodating waist and leg wearing of said pouch;
   said interlayer of vinyl/lead composed material provides a barrier to ultra-violet radiation; and
   said cloth fabric outer material layer characterized as being liquid-permeable so as to be liquid absorbent.

* * * * *